United States Patent [19]

Bodicky et al.

[11] Patent Number: 4,961,731
[45] Date of Patent: Oct. 9, 1990

[54] ANGIOGRAPHIC CATHETER WITH BALANCED DYE INJECTION OPENINGS

[75] Inventors: Raymond O. Bodicky, Oakville; Ronald Crouther, Chesterfield; LeRoy S. Forney, St. Louis; Andrew Serowski, Ballwin, all of Mo.

[73] Assignee: Sherwood Medical Company, St. Louis, Mo.

[21] Appl. No.: 204,497

[22] Filed: Jun. 9, 1988

[51] Int. Cl.$^5$ .................................. A61M 25/00
[52] U.S. Cl. .................................. 604/264; 604/280; 604/281
[58] Field of Search ............ 604/280, 281, 264; 128/656, 658

[56] References Cited

U.S. PATENT DOCUMENTS

| | | |
|---|---|---|
| 3,419,010 | 12/1968 | Williamson . |
| 3,618,614 | 11/1971 | Flynn . |
| 3,680,562 | 8/1972 | Wittes et al. . |
| 3,828,767 | 8/1974 | Spiroff . |
| 3,890,977 | 6/1976 | Wilson . |
| 3,938,501 | 2/1976 | Erikson . |
| 4,033,331 | 7/1977 | Guss et al. . |
| 4,117,836 | 10/1978 | Erikson . |
| 4,169,464 | 10/1979 | Obrez . |
| 4,250,072 | 2/1981 | flynn . |
| 4,279,252 | 7/1981 | Martin . |
| 4,385,635 | 5/1983 | Ruiz . |
| 4,563,181 | 1/1986 | Wijayarathna et al. . |
| 4,568,338 | 2/1986 | Todd . |
| 4,573,476 | 5/1986 | Ruiz . |
| 4,694,838 | 9/1987 | Wijayarthna et al. . |
| 4,735,620 | 4/1988 | Ruiz . |
| 4,747,840 | 5/1988 | Ladika ................... 604/281 |

FOREIGN PATENT DOCUMENTS 3309052.1  9/1984  Fed. Rep. of Germany .

Primary Examiner—Stephen C. Pellegrino
Attorney, Agent, or Firm—Andrew J. Beck; Montgomery W. Smith; Richard D. Allison

[57] ABSTRACT

An improved non-whip angiographic catheter has a preselected number of openings of preselected size, location and orientation along the straight portion of the catheter near the distal tip so as to distribute the force of the high-pressure dye injection jets while maintaining the non-whip characteristic. At least one opening in the catheter long portion is provided facing the open end of the tip portion so that the dye trajectories from the catheter tip opening and the catheter long portion opening are generally coplanar and perpendicular so as to interfere with each other for improved dye dispersion. At least two reaction openings of predetermined size are provided on the opposite side of the catheter long portion at preselected locations, the dye trajectories of these three reaction openings also being generally coplanar with the trajectories of the first opening and the open end of the catheter tip. The special openings have sufficiently small diameters and are specially staggered so as to reduce the possibility of kinking the catheter during placement of the catheter into position for diagnostic angiography.

14 Claims, 2 Drawing Sheets

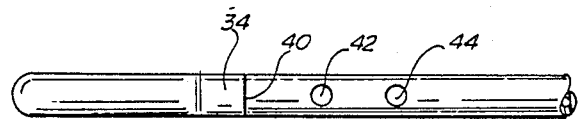
Fig. 1.
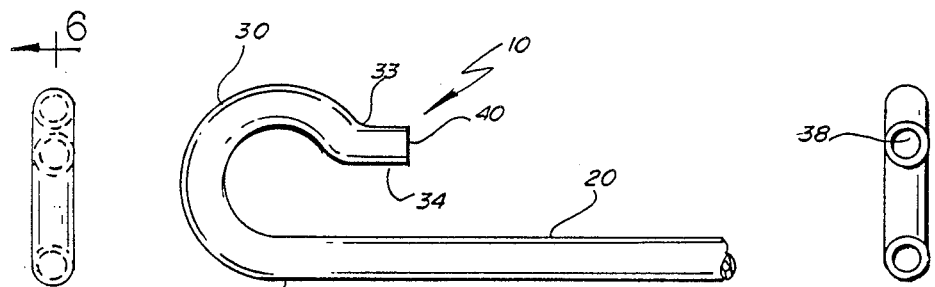
Fig. 2.
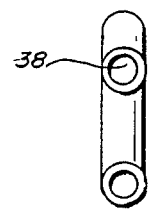
Fig. 4.
Fig. 3.
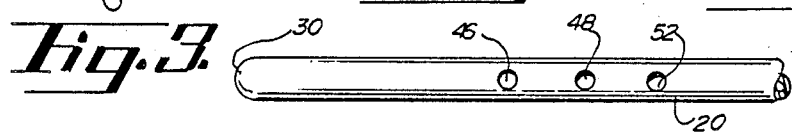
Fig. 5.
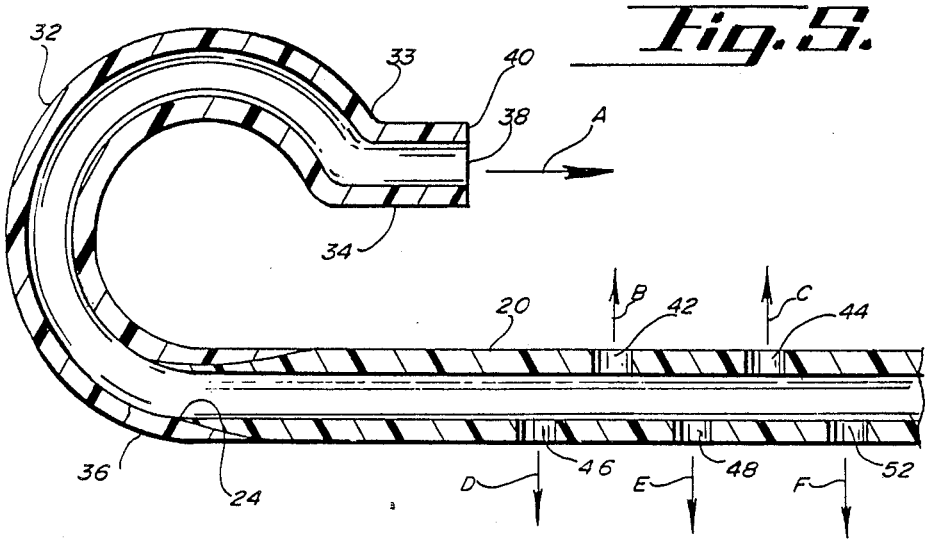
Fig. 6.

ANGIOGRAPHIC CATHETER WITH BALANCED DYE INJECTION OPENINGS

BACKGROUND OF THE INVENTION a. Field of the Invention

The invention relates generally to angiographic catheters for injecting a radiopaque material or contrast medium into arteries and/or the heart, for radiological diagnostic purposes. More specifically, the invention relates to an angiographic catheter having a preselected number of dye injection openings of predetermined size, location and orientation so as to provide improved dynamic stability of the catheter during high-pressure ventricular angiography so as to minimize the potential risk of causing ectopic beats or fibrillation, and also to improve reliability of the angiographic diagnosis.

b. Description of the Prior Art

In coronary angiography, a tip of a catheter is inserted into a brachial, axillary or femoral artery and from there advanced into the portion of the aorta proximal to the coronary ostia.

With certain catheters, after the coronary arteries are located, radiopaque dye is injected for visualization of those arteries. In ventricular angiography, the catheter tip of, for example, a femoral ventricular catheter is advanced further into the heart, and the dye is then injected for radiographic visualization. The dye may be injected at volumetric flow rates of, e.g., ten to twenty milliliters per second for several seconds, and at relatively high pressures on the order of about one thousand pounds per square inch (psi) or more, with a pressure rise time of about 0.5 second, as is customary. Maximum peak fluid pressures may reach or exceed 1,300 psi.

Various shapes and designs have been proposed and used for ventricular angiography. For example, a catheter may be a generally straight catheter with an open end and a plurality of spaced sidewall openings adjacent the open end. In one type of loop catheter commonly described as a having a "pigtail" shape, a loop is formed on the distal end portion of the catheter, extending in a plane including the long axis of the catheter. Holes through the outer wall proximal to the loop and at the end of the catheter produce a dispersed pattern of dye injection.

It is known, however, that movement of the catheter tip during angiography adversely affects the utility of the diagnostic procedure. Furthermore, in some instances the catheter tip movement may be potentially harmful to the patient because the tip may impact the heart or vessel walls potentially causing fibrillation, asystole or arrhythmia, or may even dislodge an arteriosclerotic plaque. Because a significant proportion of patients undergoing diagnostic coronary angiography are found to have no significant coronary artery disease, there is a general need to reduce risks to the patients which arise solely from the diagnostic techniques employed.

In a configuration directed to the problem of catheter tip movement, a non-whip catheter is disclosed in U.S. Pat. No. 4,736,620, issued to Oscar F. Ruiz. The "non-whip" catheter includes a curved end resembling the general shape of a shepherd's staff or hook, wherein the open end of the distal tip faces back in the direction of the catheter A first opening in the catheter sidewall opposed and spaced from the distal tip directs an interfering stream of dye at the main stream exiting from the tip for stream breakup and mixing. A second opening in the catheter sidewall on the opposite side of the catheter from the first sidewall opening provides a reaction force so as to prevent movement of the catheter at the moment of dye injection.

While the design of U.S. Pat. No. 4,736,620 represents an improvement over previous catheter designs, it has been found the dye exiting the reaction force opening of the non-whip catheter can stimulate the coronary walls so as to create the potential for random ectopic beats or minor ventricular fibrillation so as to render the angiogram non-diagnostic. In other instances, the strength of the reaction force jet may cause turbulence or other undesirable flow patterns within the blood vessel or the heart so as to reduce the diagnostic value of the angiogram.

SUMMARY OF THE INVENTION

The invention is summarized in an improved non-whip angiographic catheter having a preselected number of openings of preselected size, location and orientation along the straight portion of the catheter near the distal tip so as to distribute the force of the high-pressure dye injection jets while maintaining the non-whip characteristic. At least one opening in the catheter long portion is provided facing the open end of the tip portion so that the dye trajectories from the catheter tip opening and the catheter long portion opening are generally coplanar and perpendicular so as to interfere with each other for improved dye dispersion. At least two reaction openings of predetermined size are provided on the opposite side of the catheter long portion at preselected locations, the dye trajectories of these three reaction openings also being generally coplanar with the trajectories of the first opening and the open end of the catheter tip. The special openings have sufficiently small diameters and are specially staggered so as to reduce the possibility of kinking the catheter during placement of the catheter into position for diagnostic angiography.

It is a broad object of this invention to provide an improved non-whip angiographic catheter which is dynamically stable in operation and which minimizes undesirable effects of high-pressure, large volume dye flows from the catheter Another object of this invention to provide an angiographic catheter which has improved resistance to kinking during placement into the heart or artery for diagnostic angiography.

Other objects, features and advantages of the invention will be readily apparent from the following detailed description and the accompanying drawings.

BRIEF DESCRIPTION OF THE DRAWINGS

FIG. 1 is a partial top view of a preferred embodiment of the improved angiographic catheter according to the invention.

FIG. 2 is a side view of FIG. 1.

FIG. 3 is an end view of FIG. 2, from the left.

FIG. 4 is an end view of FIG. 2, from the right.

FIG. 5 bottom view of FIG. 1.

FIG. 6 is a partial enlarged cross section of FIG. 2 taken along the line 6—6 of FIG. 3.

DESCRIPTION OF THE PREFERRED EMBODIMENT

Figure 7:
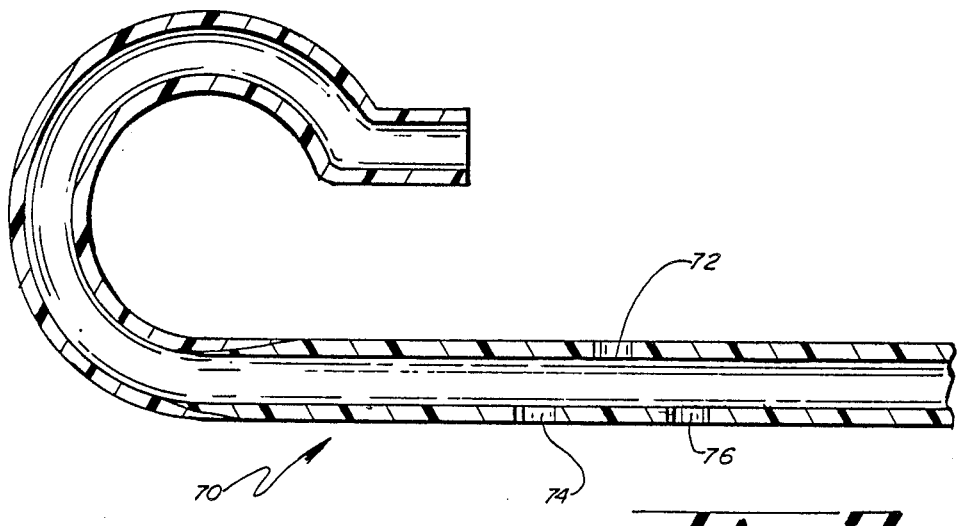
FIG. 7 is a partial enlarged cross section of another embodiment of an angiographic catheter according to the principles of the invention.

As shown in FIGS. 1-6, a preferred embodiment of a catheter 10, in accordance with the invention, has a long flexible tubular portion 20 constructed from a suitable plastic tubing stock such as singly extruded, coextruded, or braided catheter tubing. The plastic tubing stock is preferably a coextruded polyamide and polyurethane, and is selected to give the catheter the desired torque and column strength necessary to push and rotate the catheter while inserting and placing the catheter in position in the patient's heart or coronary artery or other blood vessel, and also so as to be sufficiently strong to withstand high-pressure fluid injection at pressures on the order of 1000 pounds per square inch. While the long portion 20 is shown as being straight, it will be readily understood by those skilled in the art that various curvatures of relatively large radius may be formed therein to aid in insertion and/or positioning of the catheter.

At one end 22 of the long portion 20 is an end portion 30 comprising a generally circularly-shaped curved portion 32 and a substantially straight tip portion 34, a bend 33 of small radius separating the curved portion 32 from the tip portion 34. It will be understood that the particular bend radius used may be larger or smaller for the convenience of manufacture. As shown, the curved portion 32 extends in an arc of greater than 180 degrees. Again it will be understood that other shapes may be used, e.g., the tip portion 34 need not be straight but instead may be a curved section, or it may be desired that the curved portion 32 is not generally circular but is instead elliptical or otherwise smoothly curved.

The end portion 30 is preferably constructed from a suitable plastic tubing stock as well. The end portion 30 should be softer and more flexible than the long portion 20, and may be made so by using a softer plastic material, such as polyurethane alone, or by using tubing stock of reduced wall thickness. As shown in FIG. 6, the end portion 30 has a region 36 of gradually increasing inside diameter which is attached, fused, drawn over or coextruded onto a region 24 of the long portion 20 of gradually tapered outside diameter.

The outside diameter of the catheter tubing is generally in the range from 4 to 8 French (0.052 to 0.106 inch) with an inside diameter selected from the range of approximately 0.030 to 0.080 inch. In particular, for the long portion 20, an outside diameter of about 5 French (0.066 inch) and an inside diameter of about 0.046 inch is preferred. For the end portion 30, an outside diameter of about 5 French (0.066 inch) and an inside diameter of about 0.041 inch is preferred. The total length of the catheter is generally in the range from 50 to 120 cm, and is preferably about 65 cm for a brachial or axillary approach or about 100-110 cm for a femoral approach.

As shown in FIGS. 2, 4 and 5, the tip portion 34 has an opening 38 at the distal end thereof for passage of a first stream of fluid under pressure from the catheter into the blood vessel in which the catheter is positioned. The tip portion 34 is shaped and the opening 38 positioned so that the first stream exits the tip portion 34 spaced away from and doubled back in a direction generally parallel to the longitudinal axis of the long portion 20, as illustrated by the arrow marked "A" in FIG. 6. Fluid flow in the direction marked "A" is seen after the catheter has been passed over a guidewire, as is routine in the procedure of placing the catheter into position, because the guidewire imparts a predetermined inelastic deformation to the shape of the end portion 30.

It is understood by those in the art that the catheter long portion 20 is generally not straight over any large distance more than a few centimeters. Thus it should be understood that, in the context of this specification, the "generally parallel" flow from the tip portion opening 38 is only locally parallel to the long portion longitudinal axis near the distal end of the catheter. Furthermore, it will be understood that deviations from true parallel are encompassed by the invention, such as might occur when radiopaque dye is injected at higher pressures and flow rates, wherein the curved portion 30 has a tendency to open or relax slightly.

According to further aspects of the invention, the long portion 20 has a plurality of openings for permitting a corresponding plurality of pressurized fluid streams to flow from the catheter into the patient's blood vessel or heart. The size, location and spacing of each of the openings is specially preselected so as to provide dynamic stability of the catheter end portion 30 during fluid injection, and so as to distribute the flow forces of the dye jets over a larger area than in prior art non-whip catheters. The wider force distribution improves the diagnostic value of an angiogram by substantially minimizing the potential for undesired ectopic beats or ventricular fibrillation due to mechanical excitation or "tickling" of the heart wall by the fluid jets.

Also according to an aspect of the invention, the diameter or size of each of the plurality of openings along the long portion 20 is preselected and the openings are staggered on opposite sides of the long portion 20 so as to prevent kinking or undue bending of the catheter during placement or movement in the patient. Such kinking may be undetectable during the angiographic procedure itself, but its noticed effect is to potentially render the catheter more difficult to maneuver or position accurately.

At least a preselected first one 42 of the plurality of openings in the long portion 20 is positioned so that its corresponding stream of fluid exits the catheter in a direction toward and substantially or generally perpendicular to the first stream exiting the tip portion opening 38, as illustrated by the arrow marked "B" in FIG. 6. Once again it is to be understood that minor variations from true perpendicularity are within the scope of the invention, and may result from relaxation of the tip shape, as before noted. It may also be the case that fluid does not exit from opening 42 perpendicularly to the catheter long portion 20, due to the fluid having a large velocity component along the long portion 20, or due to fluid flow phenomena at the opening 42 itself, the dynamics of which are not fully understood or considered important here.

In a preferred embodiment, a preselected second opening 44 is also positioned so that its corresponding stream of fluid exits the catheter in a direction toward and substantially perpendicular to the first stream exiting the tip portion opening 38, as illustrated by the arrow marked "C" in FIG. 6. The openings 42,44 are axially spaced apart along the long portion 20 by a preselected first distance of about 0.188 inch, and the first opening 42 is spaced apart from the tip opening 38, away from the end portion 30 and along the long portion axis, by about 0.188 inch.

The fluid flow paths of openings 38, 42 and 44 ("A", "B" and "C", respectively) are substantially coplanar, thus causing the fluid streams exiting these openings to interfere and mix with each other. This interference and mixing enhances dispersion of the radiopaque dye into the blood flow for opacification of the blood vessel or portion of the heart muscle being studied. While such an effect has been previously described in connection with the use of two interfering flow paths, it has been found that the effectiveness of such interference is greatly reduced when either of the paths are angularly deflected out of the plane of the other by more than 5 degrees. The addition of a third coplanar flow path increases the likelihood that stream interference and mixing will in fact occur.

At least two openings in the long portion 20 on the opposite side from the first and second openings 42,44 provide the necessary reaction flow forces to maintain dynamic stability of the catheter end portion 30 during fluid injection. Specifically according to a preferred embodiment, three reaction openings 46,48,52 are shown in FIGS. 5 and 6. A preselected third opening 48 in the long portion 20 is positioned so that its corresponding stream of fluid exits the catheter in a direction opposite and substantially parallel to the streams exiting the preselected first and second openings 42,44, as illustrated by the arrow marked "E" in FIG. 6. The predetermined location of the preselected third opening 48 is between and approximately equidistant, along the long portion longitudinal axis, from the preselected first and second openings 42,44. As in the case of the interfering flows, minor deviations from true parallelism are within the scope of the invention.

Similarly, according to the preferred embodiment of the invention now being described, preselected fourth and fifth openings 46,52 in the long portion 20 are positioned so that their corresponding streams of fluid also exit the catheter in a direction opposite and substantially parallel to the streams "B" and "C" exiting the preselected first and second openings 42,44, as illustrated by the arrows marked "D" and "F" respectively, in FIG. 6.

As is now seen in FIG. 6, all of the flow paths A,B,C,D,E,F are coplanar. This results in economy and consistency in manufacture. However, the openings 46,48,52 may be positioned in different manners to achieve the same result, that is, that the resultant force of the reaction flow paths D,E,F is generally coplanar with the interfering flow paths A,B,C. This may be achieved by angularly displacing the openings 46,48,52 about the long portion longitudinal axis in any manner such that the transverse flow force components, into and out of the plane of FIG. 6, substantially cancel out, i.e., have a zero resultant force.

The predetermined location of the preselected fourth opening 46 is spaced at the preselected first distance axially of about 0.188 inch along the long portion from the third opening 48, toward the end portion 30. The predetermined location of the preselected fifth opening 52 is also spaced at the preselected first distance axially along the long portion from the preselected third opening 48, away from the end portion 30.

As previously described, minor variations from truly parallel and perpendicular flow paths are within the scope of the invention, and are to be expected in practice due to the various factors also described above.

The size, or diameter in the case of circular openings, of each of the openings is preselected to reduce the fluid flow force from any individual opening so as to substantially reduce the potential for 'tickling' or unduly exciting the walls of the heart and thereby causing undesired fibrillation which may degrade the diagnostic value of the angiogram. The opening diameter is also specially selected to reduce the tendency of catheters having sidewall openings therethrough to kink or bend excessively during insertion or other manipulation, such as when the catheter tip is forced against the walls of the aorta and the left ventricular valve. Furthermore, as can be readily seen in FIG. 6, the openings alternate along the catheter long portion 20 between interfering and reaction flow openings, further improving resistance to kinking.

According to the preferred embodiment, the openings 42,44,46,48,52 have a diameter of about 0.030 inch. Minor variations are not considered critical. For example, the openings may be oval or elliptical without departing from the scope of the invention.

Figure 8:
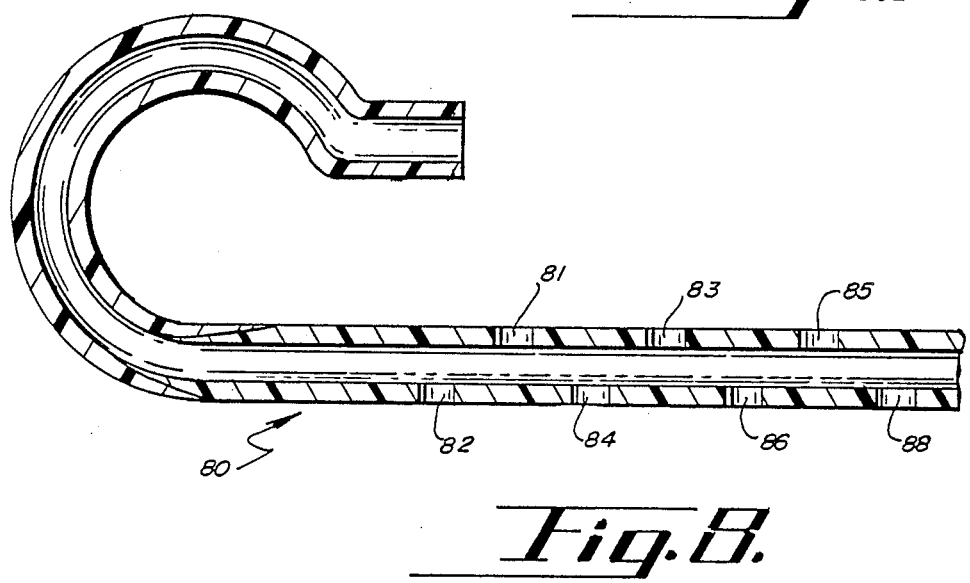
FIG. 8 is a partial enlarged cross section of still another embodiment of an angiographic catheter according to the principles of the invention.

Numerous variations and modifications, in addition to those already described, will be plain to those skilled in the art. For example, FIG. 7 shows an angiographic catheter 70 having the same shape as the just-described preferred embodiment, but the catheter 70 has only one interfering flow opening 72 and two reaction flow openings 74,76. FIG. 8 shows another alternative embodiment of an angiographic catheter 80 having three interfering flow openings 81,83,85 and four reaction flow openings 82,84,86,88.

Furthermore, the prior art pigtail-shaped catheter may also be modified according to the principles of the invention. For example, in a catheter having a loop portion at its distal end, interfering jet openings may be appropriately formed on the inside wall of the loop portion, and reaction flow openings on the outside thereof.

None of these changes depart from the basic spirit of the invention.

What is claimed is:

1. A catheter for performing diagnostic angiography on a patient comprising:

a long flexible tubular portion; and a flexible tubular end portion on one end of the long portion end portion having a first inner diameter and comprising a curved portion and a distal tip portion at an end thereof having an opening therein for passage of a first stream of fluid under pressure therethrough, the open end of the distal tip facing back in the direction of the catheter and generally parallel to the catheter, the tip opening being positioned so that the first stream exits the tip portion spaced away from and in a direction generally parallel to the long portion, the long portion having a second inner diameter wherein said second inner diameter is larger than said first inner diameter of said end portion and a plurality of openings therein for passages of e corresponding plurality of streams of fluid under pressure therethrough, the size and location and spacing of each one of said plurality of openings being preselected so as to provide dynamic stability of the end portion when the first and plurality of fluid streams pass through their respective openings, and so as to substantially minimize the potential for causing undesired heart beat patterns and undesired fluid flow patterns.

2. The catheter of claim 1, the diameter and relative spacing of each one of the plurality of openings being further preselected and said opening being further alternatively oriented with respect to each other so as to minimize kinking of the catheter during placement and maneuvering of the catheter in the patient.

3. The catheter of claim 1, wherein at least at a preselected first one of the plurality of openings generally in the long portion is oriented along an upper surface on said long portion near said tip portion opening so that its corresponding stream of fluid exits the catheter in a direction toward and substantially perpendicular to the first stream existing the tip portion opening.

4. The catheter of claim 3, wherein a preselected second one of the plurality of openings in the long portion is also positioned so that its corresponding stream of fluid exits the catheter in a direction toward and substantially perpendicular to the first stream existing the tip portion opening, the preselected second opening being axially spaced apart from the preselected first opening along the upper surface of said long portion by a predetermined first distance.

5. The catheter of claim 4, wherein a preselected third one of the plurality of openings in the long portion is positioned along the lower surface of said long portion so that its corresponding stream of fluid exits the catheter in a direction opposite and substantially parallel to the streams exiting the preselected first and second openings, and wherein the predetermined location of the preselected third opening is between and approximately equidistant, in the axial direction along the catheter long portion, from the preselected first and second openings.

6. The catheter of claim 5, wherein a preselected fourth one of the plurality of openings in the long portion is positioned on the lower surface of said long portion so that its corresponding stream of fluid also exits the catheter in a direction opposite and substantially parallel to the streams exiting the preselected first and second openings, the predetermined location of the preselected fourth opening being at the preselected first distance axially along the long portion from the preselected third opening.

7. The catheter of claim 6, wherein a preselected fifth one of the plurality of openings in the long portion is positioned on the lower surface of said long portion so that its corresponding stream of fluid also exits the catheter in a direction opposite and substantially parallel to the streams exiting the preselected first and second openings, the predetermined location of the preselected fifth opening also being at the preselected first distance axially along the long portion from the preselected fourth opening but it the opposite direction from the preselected third opening 8. The catheter of claim 7, wherein the diameter and relative spacing of each one of the plurality of openings being further preselected so as to minimize a possibility of kinking of the catheter during placement of the catheter in the patient.

9. The catheter of claim 1, wherein the curved portion of the end portion is generally circularly-shaped and extends in an arc of greater than 180 degrees and wherein the tip portion at the end of the curved portion is substantially straight, and spaced apart from and generally parallel to the long portion of the catheter.

10. The catheter of claim 1, wherein said curved portion includes an intermediate inner diameter portion which tapers from said second inner diameter to said first inner diameter.

11. A catheter for performing diagnostic angiography on a patient comprising:
 a long flexible tubular portion having upper and lower surfaces and a second inner diameter therein.
 a flexible tubular end portion on one end of the long portion, the end portion including a first inner diameter therein which is smaller than said second inner diameter and comprising a curved portion and a distal tip portion at an end thereof having an opening therein for passage of a first stream of fluid under pressure therethrough, the open end of the distal tip facing back in the direction of the catheter and generally parallel to the catheter, the tip opening being positioned so that the first stream of fluid exits the tip portion spaced away from and in a direction generally parallel to the long portion,
 the long portion having a first opening therein for passage of a second stream of fluid from the upper surface of said long portion under pressure therethrough, in a direction toward and substantially perpendicular to the first stream exiting the tip portion opening,
 the lower surface of said long portion having at least second and third openings therein for passage of third and fourth streams of fluid under pressure therethrough, respectively, in directions each opposite and substantially parallel to the second stream exiting the long portion, the second and third openings being axially positioned along the long portion about equidistant from and in opposite directions from the second opening.

12. A catheter for performing diagnostic angiography on a patient comprising:
 a long flexible tubular portion having upper and lower surfaces,
 a flexible tubular end portion on one end of the long portion, the end portion comprising a curved portion having a first inner diameter therein and a distal tip portion at an end thereof having an opening therein for passage of a first stream of fluid under pressure therethrough, the open end of the distal tip facing tack in the direction of the catheter and generally parallel to the catheter, the tip opening being positioned so that the first stream exits the tip portion spaced away from and in a direction generally parallel to the long portion,
 the long portion having a second inner diameter therein wherein said first inner diameter is smaller than said second inner diameter and a plurality of openings therein for passage of a corresponding plurality of streams of fluid under pressure therethrough, the plurality of openings being oppositely disposed in alternating fashion along the long portion, first on the lower surface of the long portion and then on the upper surface of the long portion the tip portion, so as to provide dynamic stability of the end portion when the first and plurality of fluid streams pass through their respective openings, and so as to substantially minimize the potential for causing undesired heart beat patterns and undesired fluid flow patterns, and so as to minimize kinking of the catheter during placement and measuring of the catheter in the patient.

13. The catheter of claim 12 wherein the long portion of said catheter has first, second, third, fourth and fifth openings thereon and wherein said first, third and fifth openings are disposed in a relatively spaced manner along the lower surface of the long portion and said second and fourth openings are disposed in relatively spaced manner on the upper surface of said long portion and wherein said first opening is positioned adjacent to said end portion.

14. The catheter of claim 12, wherein the diameter of said second inner diameter tapers gradually to said first inner diameter in said curved portion of the catheter to increase the flow of fluid through the openings in said long portion.

* * * * *